United States Patent
Schuetze et al.

(10) Patent No.: US 7,569,246 B2
(45) Date of Patent: Aug. 4, 2009

(54) METHOD FOR PREPARING A BIOLOGICAL MATERIAL FOR EXAMINATION UNDER A MICROSCOPE, AND CORRESPONDING ARRANGEMENT COMPRISING A BIOLOGICAL MATERIAL PREPARED USING SAID METHOD

(75) Inventors: Karin Schuetze, Tutzing (DE); Christer Busch, Uppsala (SE); Tone Bjørnsen, Tromsø (NO)

(73) Assignee: P.A.L.M. Microlaser Technologies AG, Bernried (DE)

( * ) Notice: Subject to any disclaimer, the term of this patent is extended or adjusted under 35 U.S.C. 154(b) by 577 days.

(21) Appl. No.: 10/520,418

(22) PCT Filed: Jul. 26, 2002

(86) PCT No.: PCT/EP02/08399

§ 371 (c)(1),
(2), (4) Date: Jan. 5, 2005

(87) PCT Pub. No.: WO2004/015397

PCT Pub. Date: Feb. 19, 2004

(65) Prior Publication Data

US 2005/0250219 A1    Nov. 10, 2005

(51) Int. Cl.
*G01N 1/28* (2006.01)
*B05D 3/06* (2006.01)
*C12Q 1/00* (2006.01)

(52) U.S. Cl. .............. 427/2.11; 427/289; 435/40.5; 435/40.52; 435/4; 436/174

(58) Field of Classification Search ........... 427/2.11, 427/289; 435/4; 436/174
See application file for complete search history.

(56) References Cited

U.S. PATENT DOCUMENTS

| 6,528,248 B2 * | 3/2003 | Lossing et al. ............ 435/4 |
| 2001/0028934 A1 * | 10/2001 | Baer et al. ............ 428/40.1 |

(Continued)

FOREIGN PATENT DOCUMENTS

DE    100 15 156 A1    10/2001

(Continued)

OTHER PUBLICATIONS

Qian et al., Study on Conformational Transition of EVA Random Copolymer in Selective Solvent Mixtures, European Polymer Journal, 39 (2003) pp. 375-379.*

(Continued)

*Primary Examiner*—Timothy H Meeks
*Assistant Examiner*—Cachet I Sellman
(74) *Attorney, Agent, or Firm*—Peter F. Corless; Christine C. O'Day; Edwards Angell Palmer & Dodge LLP

(57) ABSTRACT

The invention relates to a method for preparing a biological material for examination with a microscope, comprising the steps of: applying a UV laser light absorbing transparent film onto a surface of the biological material for smoothing out irregularities on the surface of the biological material in order to improve visual characteristics of the biological material; and cutting the biological material together with the UV laser light absorbing transparent film with a UV laser, thereby preparing the biological material for examination.

18 Claims, 1 Drawing Sheet

U.S. PATENT DOCUMENTS

2002/0025511 A1* 2/2002 Bova .............................. 435/4
2002/0142412 A1* 10/2002 Ogawa et al. ............ 435/173.1
2003/0180941 A1 9/2003 Schutze

FOREIGN PATENT DOCUMENTS

| EP | 0 409 550 A1 | 1/1991 |
|---|---|---|
| WO | WO-97/13838 | 4/1997 |
| WO | WO-00/66994 | 11/2000 |
| WO | WO-02/14833 A1 | 2/2002 |

OTHER PUBLICATIONS

Emmert-Buck et al., "Laser Capture Microdissection", Science, American Association for the Advancement of Science, 274(5289):998-1001 (1996).

* cited by examiner

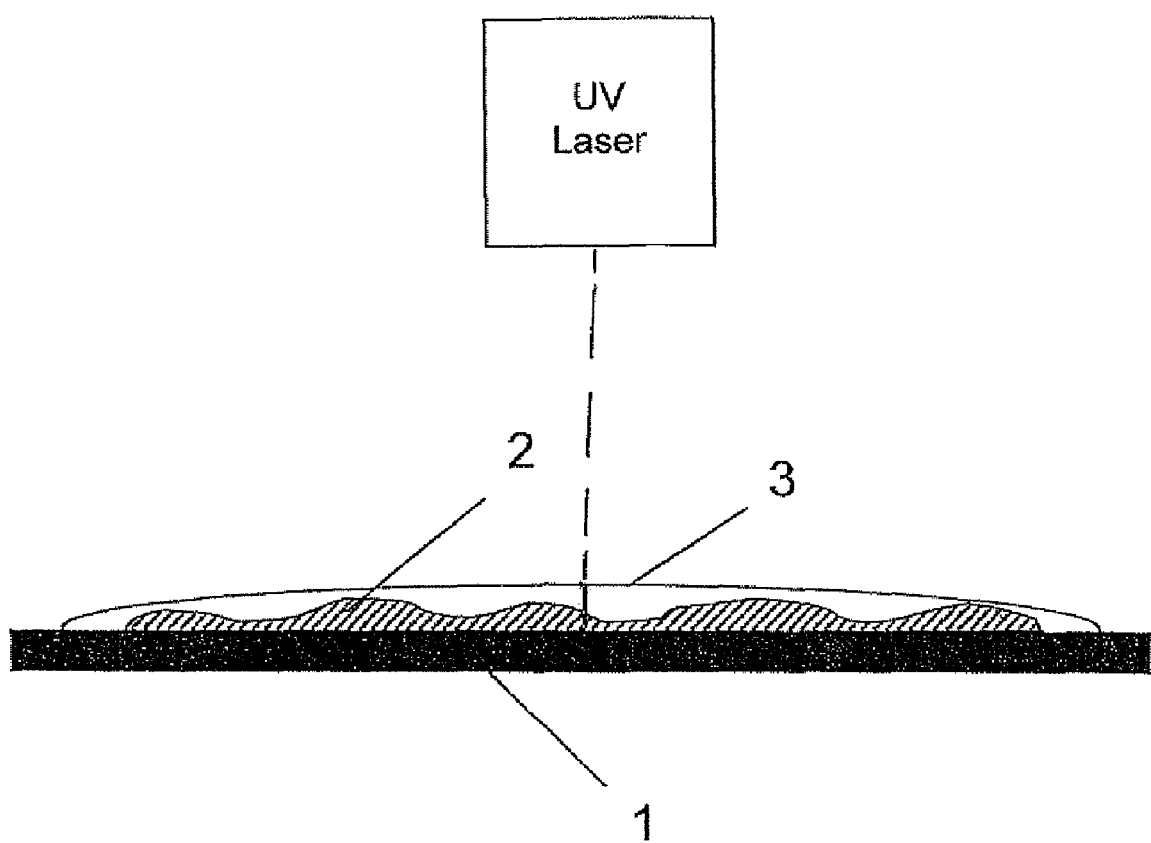

METHOD FOR PREPARING A BIOLOGICAL MATERIAL FOR EXAMINATION UNDER A MICROSCOPE, AND CORRESPONDING ARRANGEMENT COMPRISING A BIOLOGICAL MATERIAL PREPARED USING SAID METHOD

FIELD OF THE INVENTION

The present invention relates to a process for the preparation of a biological material or compound, particularly a section of tissue on an object carrier, for examination with a microscope as well as a corresponding arrangement of a biological material prepared in such a manner on carrier means, for example a glass object carrier. In particular, the present invention relates to such a process for the preparation of an examination of the biological material (in the following also described as examination material) with a laser micro-dissection system, with which individual objects can be cut and/or catapulted by means of laser radiation out of the biological material and collected in suitable receiving vessels.

BACKGROUND OF THE INVENTION

Individual objects, which are arranged on a planar object carrier, to be selected with the aid of a computer and to be processed with a laser beam are known from WO7 97/29355 A or WO 01/73398 A of the Applicant. In this case, a selected object can be separated with the aid of a computer from the surrounding mass by means of the laser beam for example, in order to release the object selected in each case from the surrounding mass. Subsequently, the released object can be catapulted by a laser-induced transport process with the aid of a laser beam, which is directed onto the released object, from the object carrier to a collecting vessel. The laser micro-dissection system therefore, apart from a microscope for examining or observing the examination material present on the respective object carrier, also comprises a laser device, which directs a laser beam, preferably a UV laser beam, onto the examination material, in order to separate and/or catapult an object, which has been previously selected, out of the surrounding examination material. Micro centrifuge or Eppendorf containers and/or the caps of such can be considered as receptacles, for example. Likewise so-called micro titration plates with a plurality of recesses or "wells" can be used as receptacles.

It is generally necessary when seperating the examination materials, which is to be examined with a microscope and prepared for subsequent processing for example, to seperate the examination material in such a manner that said examination material when observing the examination material with the microscope can be visualized in the optimum way.

In principle, however, the problem arising with biological examination materials such as, for example, tissue sections is that the examination material placed on the respective object carrier does not have a completely even surface, so that sufficiently good visual examination over the entire surface of the examination material is impossible. With laser-assisted processing of biological examination materials, in accordance with the laser dissection process of the Applicant described above for example, use of the micro-dissection system as recommended is facilitated, improved and/or only possible through the use of the mixture, preparation and/or pure substance.

SUMMARY OF THE INVENTION

The underlying object of the present invention is therefore to provide a process for preparing a biological examination material for examination with a microscope as well as an arrangement with a biological material prepared in such a manner and carrier means, on which the biological material is arranged, whereby the visual examination characteristics of the biological material are improved, so that as a result of improved visualization better and more precise observation of the biological material with the microscope is possible. In particular, the biological compound prepared with help of the present invention should also be suitable for use in a laser micro-dissection system of the kind described above, without disadvantageously affecting the visual characteristics of the material due to laser radiation.

This object is achieved in accordance with the invention by the process and/or the arrangement described herein. Certain preferred and advantageous embodiments of the present invention also are described.

In the context of the present invention, it is proposed that a transparent, i.e. translucent substance dissolved in a solvent in the form of a preparation, mixture and/or pure substance is applied onto the biological material in order to smooth out irregularities in the surface of the respective biological material, for example a tissue section, and therefore to improve visualization of the biological material and the possibility of observation with a microscope. Furthermore, the preparation, mixture and/or pure substance are constituted in such a manner that, after being applied to the surface of the examination material, it solidifies or hardens by drying, hardening or polymerization, so that a solidified film is formed preferably over the entire surface of the examination material.

As already mentioned above, irregularities in the surface of the respective examination material can be smoothed out by means of the monomer or polymer substance applied so that a substantially uniform, even surface of the examination material is obtained. The diffuse light scatter altered in such a way permits simple and precise examination of the examination material with a microscope. Furthermore, a protective film is thus formed, which protects the surface of the examination material against contamination, decomposition or degradation of examination-relevant components through dust or RNAs for example, and in addition structurally supports the entire substance to be examined, so that when individual objects are cut with a laser beam, a UV laser beam for example, no particles chip off or if catapulted with the laser beam no undesirable particles arise or chip off on the object carrier.

The substance proposed in accordance with the invention in the form of a preparation, mixture and/or pure substance is preferably constituted in such a manner that it can be applied onto the surface of the specimen as easily as possible. Therefore the transparent preparation, mixture and/or pure substance dissolved in the solvent can be constituted in the form of a spray or immersion bath for example. Likewise, the preparation, mixture and/or pure substance preferably is non- or at least hardly toxic, that is to say it is not harmful, since in the event of subsequent processing of the compound, for example, by means of laser radiation the film in its final state as well as the corresponding object released by the laser radiation remains clinging on the respective object and together with this is kept in a suitable vessel to be more closely examined afterwards by a control person. Since such samples cut or catapulted out are usually dissolved in an aqueous solution for further processing, the preparation, mixture and/or pure substance applied onto the respective examination material should also be easily soluble in aqueous solution.

Likewise, a preparation, mixture and/or pure substance is preferably used, which is constituted in such a manner that as far as possible there is no effect whatsoever on subsequent analyses, e.g. molecular analyses. As a preparation, mixture and/or pure substance according to the invention therefore harmful mixtures, preparations or pure substances preferably do not come into consideration for the examination material with the purpose of its examination, as for example short- or long-chain and/or totally or partly unsaturated acids and/or bases, poly-amides, -alcohols, -carbonates, silicones or mixtures and/or preparations thereof or similar substances, which may be used as a preparation, mixture and/or pure substance.

If the intention is to use the compound prepared in accordance with the invention in a laser micro-dissection system, the preparation, mixture and/or pure substance applied, dependent upon the wavelength of the laser used, is also preferably constituted in such a manner that the laser light emitted. by the laser is completely absorbed as far as possible by this preparation, mixture and/or pure substance in order to be able to cut or catapult out the preparation, mixture and/or pure substance including the examination material covered therewith as effectively as possible, i.e. with optimum efficiency.

As already described, the preparation, mixture and/or pure substance is dissolved in a solvent or applied directly as pure substance onto the surface of the respective examination material. As a solvent, for example, isopropanol or other short-chain alcohols, ketones, esters, water or mixtures thereof or similar substances serving as solvents with or without stabilizing agents can be used. After the solvent has evaporated or flashed off, solidification or build up of a polymer structure or polymerization may take place and thus the formation of the desired protective film, which smoothes out irregularities in the surface of the examination material. For as good observation as possible of the examination material the preparation, mixture and/or pure substance in its final state there should be a balance between the refractive index onto the examination material and its surrounding materials, resulting in a reduction of undesirable scattered light.

Since in the field of laser micro dissection, work is frequently carried out with cut sections, which are, for example, coloured with histochemical or immunological dyes, the preparation, mixture and/or pure substance is preferably also constituted in such a manner that it minimizes reciprocal effects of the laser, when such sections coloured with histochemical or immunological dyes for example are cut and consequently improves the. examination and manipulation characteristics of the examination material. The same also applies to fluorescent-coloured examination materials, whereby when the examination materials are radiated with light of a wavelength, the fluorescence in the corresponding coloured objects can be excited, in order thus to be able to determine different visual characteristics of the examination material. In particular, it is possible for example to make a distinction between malignant and benign cells of the compound examined in this way etc. Therefore, it is advantageous if substances, which for example preserve the RNA, DNA and/or proteins of the examination material and/or promote the fluorescence of the dyes in the desired way, are worked into the film to be applied onto the surface of the examination material.

The present invention is described below in detail with reference to the accompanying drawing on the basis of preferred embodiments.

BRIEF DESCRIPTION OF THE DRAWINGS

FIG. 1 illustrates an object carrier for use in accordance with the present invention, onto which the examination material and transparent film have been applied; a UV laser also is shown in order to depict an exemplary cutting of the examination material and the transparent film.

DETAILED DESCRIPTION OF THE INVENTION

In the single figure, an object carrier 1 is illustrated with examination material 2, a section of tissue applied thereon, for example. The object carrier 1 can in particular concern a conventional glass object carrier. However, a glass object carrier with a foil or membrane stretched over it, which absorbs the laser light of the laser used in each case, can also be employed so that the membrane as well as the examination material 2 present thereon is cut and possibly catapulted out into a collecting vessel. The use of such a membrane ensures that the examination material 2, cut out by the laser radiation, is transferred integrally to the collecting vessel. Finally, only one membrane or a membrane-membrane combination can also be used as an object carrier for example, whereby in the latter case the lower membrane is laser-light absorbing and serves as a carrier, while the membrane directly below the examination material 2 and the membrane present on the other membrane is laser light-absorbing and thus can be catapulted together with the examination material 2.

As also evident from the drawing, a transparent film 3 that contains non-toxic preparations, mixtures or pure substances, which are not harmful for the examination material with regard to the examination is applied onto the surface of the examination material 2. These may be short-or long-chain and/or totally or partly unsaturated acids and/or bases, poly-amides, -alcohols, -carbonates or silicones or mixtures and/or preparations thereof or similar substances, which may be used as a preparation, mixture and/or pure substance. The substances used in each case preferably should not negatively affect the examination material and/or tissue 2 and/or influence or even destroy the tissue or substances or agents introduced into the tissue for the purpose of the examination, as the result of undesirable chemical reactions, e.g. complexation, formation of radicals or other reactions.

The preparation, mixture and/or pure substance is dissolved in a solvent or applied as a pure substance onto the surface of the examination material 2, whereby this can take place in a simple and easy way by spraying as an aerosol, brushing or even by immersing the examination material in an immersion bath. Since the preparation, mixture and/or pure substance is applied in a liquid state or as an aerosol onto the surface of the examination material 2, the corresponding liquid or aerosol can penetrate the irregularities, formed in the surface of the examination material 2 as illustrated in the drawing, and thus smooth these out. Through appropriate measures, the examination material changes from its initial state, in which the preparation, mixture and/or pure substance is present at a very great distance between the individual polymer strands or in a "de-convoluted" condition, into its final state, in which the polymer strands develop, diversify, for example "convolute" or "fray". The preparation, mixture. and/or pure substance solidifies by evaporation of the-solvent content or by reaction, so that the film 3 applied onto the surface of the examination material 2 solidifies and dries throughout, i.e. a type of through hardening of the film 3 takes place. It should be noted however it is not essential that an absolutely dry and mechanically very solid state has to be assumed. It is already sufficient if solidification and/or consolidation of the film 3 takes place in such a manner that cutting and catapulting out with a laser is possible, i.e. it is enough if the film 3 is dry and solidified so that it is no longer tacky for example.

Since after the solvent has evaporated the polymer structure solidifies and thus the protective film 3 forms. on the examination material 2, which in particular smoothes out irregularities in the surface of the examination material 2 and thus improves the visual quality of the examination material 2, the preparation, mixture and/or pure substance should be constituted in such a manner that in its polymerized and/or consolidated or solidified and substantially solvent-free structure it permits optimum visual characteristics for the precise visual examination of the examination material 2 with a microscope, in a laser micro-dissection system for example. This happens for example through lateral homogenization of the optical path through the examination material. Ideally, minimization or prevention of undesirable scattered light and balancing of the refractive index onto the material surrounding the examination material, such as, for example, the carrier membrane or the glass object carrier, take place.

As commercial products, which can be employed in the context of the present invention for producing the protective film 3, the following preparations sold under the brand names "Formvar " ®or "PinPoint " ®can be used for example. Particularly advantageous is the use of the preparation. sold under the brand name "Gum Rosin " ®, which fulfills all characteristics and/or requirements described herein on the preparation and particularly facilitates effective smoothing out of irregularities in the respective tissue section and/or examination material 2 and thus makes possible substantially improved visualization and in addition is simple to apply, being easily soluble in aqueous medium. Furthermore, the latter preparation is also constituted in such a manner that in no way it affects subsequent molecular analyses, and due to its absorptive properties with regard to UV laser light can be very easily cut or catapulted in its final state with a UV laser. The resin composition of the preparation "Gum Rosin"® approximately as follows:

Resinous acid content:

| | |
|---|---|
| Abietic acid | 18% |
| Levopimaric acid | 32% |
| Neoabietic acid | 11% |
| Palustric acid | 12% |
| Pimaric acid | 9% |
| Isopimaric acid | 3% |
| Others | 5% |
| Neutral content: | 10% |

In the field of laser micro-dissection cut out and/or catapulted samples are usually dissolved in aqueous solution (buffer medium of the most varied kind, depending upon the analysis required) for subsequent processing. Therefore, it is generally desirable if the protective film 3 applied onto the surface of the examination material 2 is easily soluble in aqueous medium.

As already described above when cutting and/or catapulting out samples in a laser micro-dissection system, reciprocal effects between the laser used and the sample can arise in such a manner that certain visual characteristics of the sample, which are necessary for subsequent molecular analyses etc.

are affected or altered. Thus, for such molecular analyses sections are frequently coloured with histochemical or immunological dyes for example, or fluorescent-coloured compounds are used for example, whereby the fluorescence of the compound is evaluated during the subsequent analysis of the compound. When cutting such compounds by means of a laser, the effect of the fluorescence and of the dyes as well as for example the RNA, DNA or proteins of the compound are impaired.

Therefore, it is advantageous if the mixture, preparation or pure substance 3 applied onto the surface of the examination material 2 contains substances preserving or otherwise improving the visual characteristics of the examination material. In particular substances, which preserve the RNA ("ribonucleic acid") and/or substances, which promote the fluorescence characteristics of the dyes or generally the effect of the dyes, that is to say influence these in the desired way, are suitable.

For example, in order to preserve the RNA of the examination material 2, the protective film 3 can contain in particular a substance sold under the brand name RNAlater® by the Ambion company, whereby this concerns an RNA stabilizing agent. Likewise, similar RNA preserving agents, which are based for example on ammonium sulfate in an aqueous solution can be used.

Concerning the substances for preserving and/or achieving the desired fluorescence visual characteristics of the compound, both fluorophors, i.e. dyes, which emit light of other wavelength(s) for excitement with defined excitation wavelengths, as well as so-called "quenchers " i.e. agents, which prevent fluorescence emission with certain light wavelengths by de-excitation onto radiation-less channels, into which the mixture, preparation or pure substance forming the protective film 3 are directed. "Quenchers" in the actual physico-chemical sense are substances, which due to their electronic structure can very easily absorb energy and then give off this energy without radiation or release this energy onto other de-excitation channels, which is not harmful to tissues or molecules. Examples of such quenchers, which can be used in the protective film 3, are ketones such as dimethylketone, dimethylamine, phenylmethylketone or acetyl naphtalene. The quenchers specified above are used in the protective film 3 particularly if the application of energy by the laser used. is so great that due to energy transfer to other molecules, for example the macromolecule DNA, RNA or proteins, these could be destroyed by direct bond splitting, conformation change or other alterations in the primary, tertiary or quaternary structure or could be affected unfavourably for subsequent examinations.

In particular quenchers, which by quenching in the sense of a Stern Vollmer analysis prevent the fluorescence substantially more effectively with regard to bimolecular quenching than its self de-excitation permits with inherent uni-molecular kinetics, are used within the scope of the present invention. This means that the fluorescence life span in the presence of the quencher substance is significantly shorter than if the quencher substance were absent. Implicitly, higher molecular kinetics are also included in these assumptions.

Although the present invention has been described above on the basis of the preferred scope of application for preparing a biological examination material or compound 2, naturally application of the process described above to other (organic or inorganic) examination materials, particularly also non biological examination materials, in order to optimize the visual characteristics for subsequent examination with a microscope, is also in principle conceivable.

The invention claimed is:

1. A process for preparing a biological material for examination with a microscope, comprising the steps of:
   applying a UV laser light absorbing transparent film onto a surface of the biological material for smoothing out irregularities on the surface of the biological material in order to improve visual characteristics of the biological material; and
   cutting the biological material together with the UV laser light absorbing transparent film with a UV laser, thereby preparing the biological material for examination.

2. The process of claim 1, wherein the film is sprayed onto the surface of the biological material.

3. The process of claim 1, wherein the film is brushed onto the surface of the biological material.

4. The process of claim 1, wherein the film is applied onto the surface of the biological material by immersing the biological material in an immersion bath.

5. The process of claim 1, wherein the film is not toxic.

6. The process of claim 1, wherein the film is inert and when applied onto the biological material the biological material is not disadvantageously affected chemically or biologically.

7. The process of claim 1, wherein the film contains a transparent preparation, mixture and/or pure substance.

8. The process of claim 7, wherein the preparation, mixture or pure substance is a preparation, mixture and/or pure substance selected from the group of short- or long-chain and/or totally or partly unsaturated acids and/or bases, poly-amides, -alcohols, - carbonates or silicones or mixtures thereof.

9. The process of claim 1, wherein the film when applied onto the surface of the biological material has a character promoting the visual characteristics of the biological material with regard to balance of the refractive index, suppression of undesirable light scattering and/or improved visualization of the biological specimen.

10. The process of claim 1, wherein the film has a preparation, mixture and/or pure substance soluble in an aqueous solution.

11. The process of claim 1, wherein the film contains at least one substance for systematically affecting the visual characteristics of the biological material when radiated with light.

12. The process of claim 11, wherein the film contains at least one substance preserving the RNA of the biological material when radiated with light.

13. The process of claim 11, wherein the film contains at least one substance systematically affecting the fluorescence visual characteristics of the biological material.

14. The process of claim 13, wherein the film contains a fluorophor for achieving a fluorescence with a certain light wavelength.

15. The process of claim 13, wherein the film contains at least one substance, which prevents fluorescence with a certain light wavelength.

16. The process of claim 15, wherein the substance is selected for prevention of fluorescence in such a manner that it prevents the fluorescence with the certain light wavelength by quenching in the sense of a Stern Vollmer analysis substantially more effectively with regard to bimolecular quenching than its self de-excitation permits with inherent uni-molecular kinetics.

17. The process of claim 1, wherein the film has a preparation, mixture and/or pure substance dissolved in a solvent, which is carried on the surface of the biological material.

18. The process of claim 17 whereby the solvent, in which the preparation, mixture and/or pure substance is dissolved, is a solvent selected from the group of short-chain alcohols, ketones, esters, benzenes or water.

* * * * *